(12) United States Patent
Keggi et al.

(10) Patent No.: US 9,271,840 B2
(45) Date of Patent: Mar. 1, 2016

(54) LOW STRESS ALL POLY TIBIAL COMPONENT

(76) Inventors: John Keggi, Woodbury, CT (US); Louis Keppler, Valley City, OH (US); Timothy McTighe, Chagrin Falls, OH (US); Declan Brazil, Chatswood (AU); Carl Knobloch, East Taunton, MA (US)

( * ) Notice: Subject to any disclaimer, the term of this patent is extended or adjusted under 35 U.S.C. 154(b) by 0 days.

(21) Appl. No.: 13/346,623

(22) Filed: Jan. 9, 2012

(65) Prior Publication Data
US 2012/0109324 A1 May 3, 2012

Related U.S. Application Data

(63) Continuation-in-part of application No. 13/189,487, filed on Jul. 22, 2011, now abandoned, which is a continuation of application No. 13/045,458, filed on Mar. 10, 2011, now abandoned.

(60) Provisional application No. 61/312,652, filed on Mar. 10, 2010.

(51) Int. Cl.
*A61F 2/38* (2006.01)
*A61B 17/16* (2006.01)
*A61B 17/17* (2006.01)
*A61B 17/00* (2006.01)
*A61F 2/30* (2006.01)
*A61F 2/46* (2006.01)

(52) U.S. Cl.
CPC ............. *A61F 2/389* (2013.01); *A61B 17/1675* (2013.01); *A61B 17/1764* (2013.01); *A61B 17/00234* (2013.01); *A61F 2002/30878* (2013.01); *A61F 2002/30884* (2013.01); *A61F 2002/4635* (2013.01)

(58) Field of Classification Search
CPC ....................... A61F 2/389; A61F 2002/30884
USPC ....................................................... 623/20.34
See application file for complete search history.

(56) References Cited

U.S. PATENT DOCUMENTS

| | | | |
|---|---|---|---|
| 4,215,439 A | 8/1980 | Gold et al. | |
| 4,822,362 A * | 4/1989 | Walker et al. | 623/20.32 |
| 5,405,395 A | 4/1995 | Coates | |
| 5,509,934 A * | 4/1996 | Cohen | 623/20.32 |
| 6,071,311 A | 6/2000 | O'Neil et al. | |
| 6,926,738 B2 | 8/2005 | Wyss | |
| 7,070,622 B1 | 7/2006 | Brown et al. | |
| 7,077,867 B1 | 7/2006 | Pope et al. | |

(Continued)

FOREIGN PATENT DOCUMENTS

| | | |
|---|---|---|
| EP | 0531250 | 3/1993 |
| EP | 1095637 | 5/2001 |
| GB | 1485681 | 9/1977 |

*Primary Examiner* — Brian Dukert
(74) *Attorney, Agent, or Firm* — Clayton, Howarth & Cannon, P.C.

(57) ABSTRACT

A tibial component for use in conjunction with a knee replacement surgery. An inferior surface of the tibial component may be concave to thereby improve bonding between the tibial component and a tibia. The tibial component may produce low stress in the cement mantle during in-vivo loading. A stem extending from the inferior surface of the tibial component may include an anterior curvature to facilitate the use of minimally evasive surgical techniques. The stem may further include medial-lateral wing portions with a posterior curvature to provide improved support.

38 Claims, 7 Drawing Sheets

(56) References Cited

U.S. PATENT DOCUMENTS

| | | |
|---|---|---|
| 7,344,541 B2 | 3/2008 | Haines et al. |
| 7,387,644 B2 | 6/2008 | Beynnon et al. |
| 7,422,605 B2 | 9/2008 | Burstein et al. |
| 7,524,334 B2 | 4/2009 | Haidukewych |
| 7,572,292 B2 | 8/2009 | Crabtree et al. |
| 7,628,794 B2 | 12/2009 | Stumpo et al. |
| 7,695,477 B2 | 4/2010 | Creger et al. |
| 7,708,782 B2 | 5/2010 | Burstein et al. |
| 2008/0183177 A1* | 7/2008 | Fox et al. .................. 606/88 |

* cited by examiner

LOW STRESS ALL POLY TIBIAL COMPONENT

CROSS-REFERENCE TO RELATED APPLICATIONS

This application is a continuation in part of U.S. patent application Ser. No. 13/189,487, filed Jul. 22, 2011, which is a continuation of U.S. patent application Ser. No. 13/045,458, filed Mar. 10, 2011, which claims the benefit of U.S. Provisional Application No. 61/312,652, filed Mar. 10, 2010, which are all hereby incorporated by reference herein in their entireties, including but not limited to those portions that specifically appear hereinafter, the incorporation by reference being made with the following exception: In the event that any portion of the above-referenced applications is inconsistent with this application, this application supercedes said above-referenced applications.

STATEMENT REGARDING FEDERALLY SPONSORED RESEARCH OR DEVELOPMENT

Not Applicable.

BACKGROUND

1. The Field of the Present Disclosure

The present disclosure relates generally to prostheses and more particularly, but not necessarily entirely, to knee joint prostheses and to a method of installing knee joint prostheses during a knee replacement surgery.

2. Description of Related Art

Knee joint replacement surgery involves replacing a knee joint with an artificial knee joint, referred to sometimes herein as a "prosthesis" or "implant." Artificial knees may comprise a tibial component and a femoral component. To begin a knee joint replacement, a surgeon may make an incision on the front of the knee to allow access to the joint. Several different approaches may be utilized to make the incision. Once the knee joint is opened, the surgeon may prepare the end of the femur bone to receive the femoral component by making one or more cuts to the bone. A cutting guide may be utilized to ensure proper alignment. The femoral component may then be installed onto the end of the femur. The femoral component may replace the bottom surface of the femur bone and the groove where the patella sits.

Next, the surface of the tibia bone may be prepared for receiving the tibial component. In particular, the top of the tibia may be removed by the surgeon leaving a relatively flat surface. The tibial component may include a stem that is then inserted into the tibia. Bone cement may be utilized to secure the tibial component to the tibia. The tibial component may replace the top surface of the tibia bone. The tibial component may include a surface for receiving the femoral component. The surgeon may then close the incision.

Several shortcomings exist for the previously available tibial components. For example, the stem geometry for previously available tibial components have not been overly conducive to minimally invasive surgery (MIS). That is, previously available tibial components included stems that required extensive displacement of tissue during surgery in order to install the stems into the tibia bone. This extensive displacement of tissue led directly to increased patient recovery time.

Another shortcoming of previously available tibial components is that their design could lead to failure of the bond between the tibia component and the tibia. For example, some previously available tibial components included undercut cement grooves and channels that were utilized to anchor the components using bone cement. Disadvantageously, these grooves and channels produced non-uniform stress fields during in-vivo loading that loosened the tibial components from the tibia.

The prior art is thus characterized by several disadvantages that are addressed by the present disclosure. The present disclosure minimizes, and in some aspects eliminates, the above-mentioned failures, and other problems, by utilizing the methods and structural features described herein.

The features and advantages of the present disclosure will be set forth in the description which follows, and in part will be apparent from the description, or may be learned by the practice of the present disclosure without undue experimentation. The features and advantages of the present disclosure may be realized and obtained by means of the instruments and combinations particularly pointed out in the appended claims.

BRIEF DESCRIPTION OF THE DRAWINGS

The features and advantages of the disclosure will become apparent from a consideration of the subsequent detailed description presented in connection with the accompanying drawings in which.

DETAILED DESCRIPTION

Figure 1A:
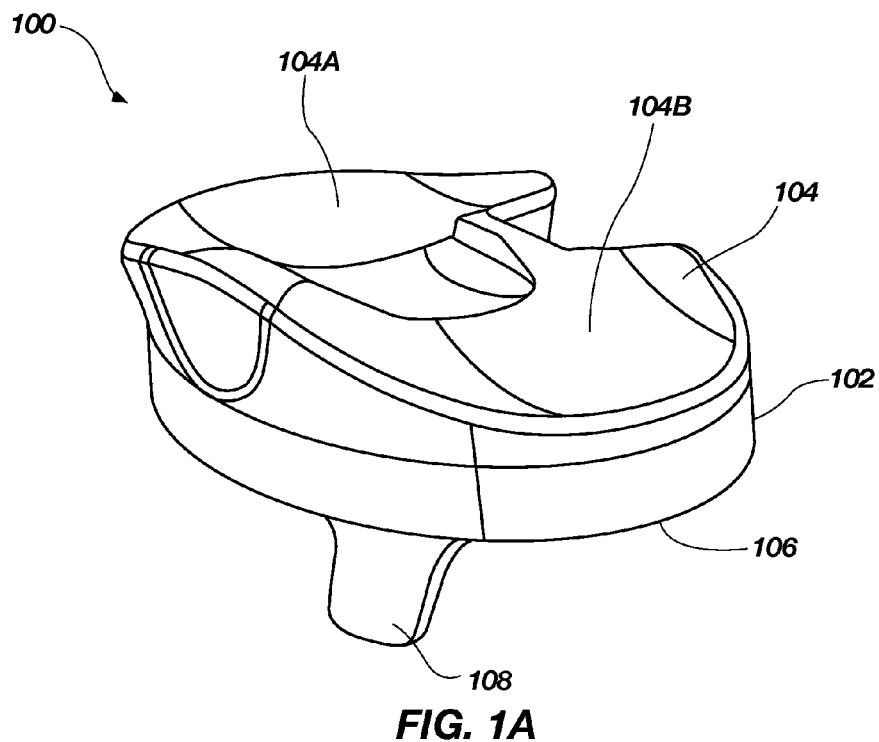
FIG. 1A is a perspective view of a tibial component in accordance with an embodiment of the present disclosure.

For the purposes of promoting an understanding of the principles in accordance with the disclosure, reference will now be made to the embodiments illustrated in the drawings and specific language will be used to describe the same. It will nevertheless be understood that no limitation of the scope of the disclosure is thereby intended. Any alterations and further modifications of the inventive features illustrated herein, and any additional applications of the principles of the disclosure as illustrated herein, which would normally occur to one skilled in the relevant art and having possession of this disclosure, are to be considered within the scope of the disclosure claimed.

It must be noted that, as used in this specification and the appended claims, the singular forms "a," "an," and "the" include plural referents unless the context clearly dictates otherwise. In describing and claiming the present disclosure, the following terminology will be used in accordance with the definitions set out below. As used herein, the terms "comprising," "having," "including," "containing," "characterized by," and grammatical equivalents thereof are inclusive or open-ended terms that do not exclude additional, unrecited elements or method steps.

As used herein, the term "anterior" may refer the front plane of the human body, e.g., a patient. Parts of prostheses labeled as "anterior" or "extending anteriorly" means that after implantation, those parts face or extend towards the anterior of the patient. As used herein, the term "posterior" may refer the back plane of the human body, e.g., a patient. Parts of prostheses labeled as "posterior" or "extending posteriorly" means that after implantation, those parts face or extend towards the posterior of the patient.

Applicant has discovered a novel tibial component or prosthesis for use in a knee replacement surgery. An embodiment of the present disclosure may include a tibial component having a unique stem geometry that is conducive to minimally evasive surgery techniques. An embodiment of the present disclosure may include a tibial component having a more uniform stress field during in-vivo loading. An embodiment of the present disclosure may include a tibial component having an improved bond with the tibia.

An embodiment of the present disclosure may include a tibial component having a bearing surface for receiving a femoral component attached to an end of a femur bone, and an inferior surface opposite the bearing surface, and a stem extending downwardly and anteriorly from the inferior surface to a terminal end. An embodiment of the present disclosure may include a tibial component with a stem having an anterior curvature residing in an anterior to posterior plane bisecting the tibial component, where the anterior to posterior plane is perpendicular to the anterior plane and the posterior plane of the patient.

An embodiment of the present disclosure may include a tibial component having a body with a top and a bottom, wherein a bearing surface is formed on the top of the body and an inferior surface is formed on the bottom of the body. An embodiment of the present disclosure may include a tibial component having a bearing surface with a first concave bearing surface and a second concave bearing surface for receiving a pair of condylar articular surfaces of a femoral component or the femoral bone. An embodiment of the present disclosure may include a tibial component comprising a body of unitary construction. An embodiment of the present disclosure may include a tibial component having a stem with a T-shaped cross-section.

An embodiment of the present disclosure may include a tibial component having a stem with a anteriorly facing surface extending between an inferior surface and a terminal end, the anteriorly facing surface may comprise a concave portion, also referred to herein as an "anterior curve forming a concave, anterior-facing space," also referred to herein as a stem that is "curving anteriorly." An embodiment of the present disclosure may include a tibial component having a stem extending downwardly from an inferior surface, wherein the stem may comprise a pair of laterally extending wing portions that curve in the posterior direction.

An embodiment of the present disclosure may include a tibial component having an inferior surface with a concave portion. An embodiment of the present disclosure may include a tibial component having an inferior surface with a concave portion, wherein a rim circumscribes the concave surface, or a portion of the concave surface.

An embodiment of the present disclosure may include forming a cavity in a prepared surface of a tibia, wherein the cavity extends downwardly from the prepared surface of the tibia. The cavity may include an anterior curvature. An embodiment of the present disclosure may include forming a convex or conical cement mantel between an inferior surface of a tibial component and a prepared surface of a tibia.

An embodiment of the present disclosure may include an apparatus for forming a cavity in a prepared surface of a tibia. The apparatus may include a block portion that attaches to the anterior of the tibia bone. A pivot arm may be pivotably connected to the block portion. A punch extending from the free end of the pivot arm may form the cavity when the pivot arm is rotated.

Figure 1B:
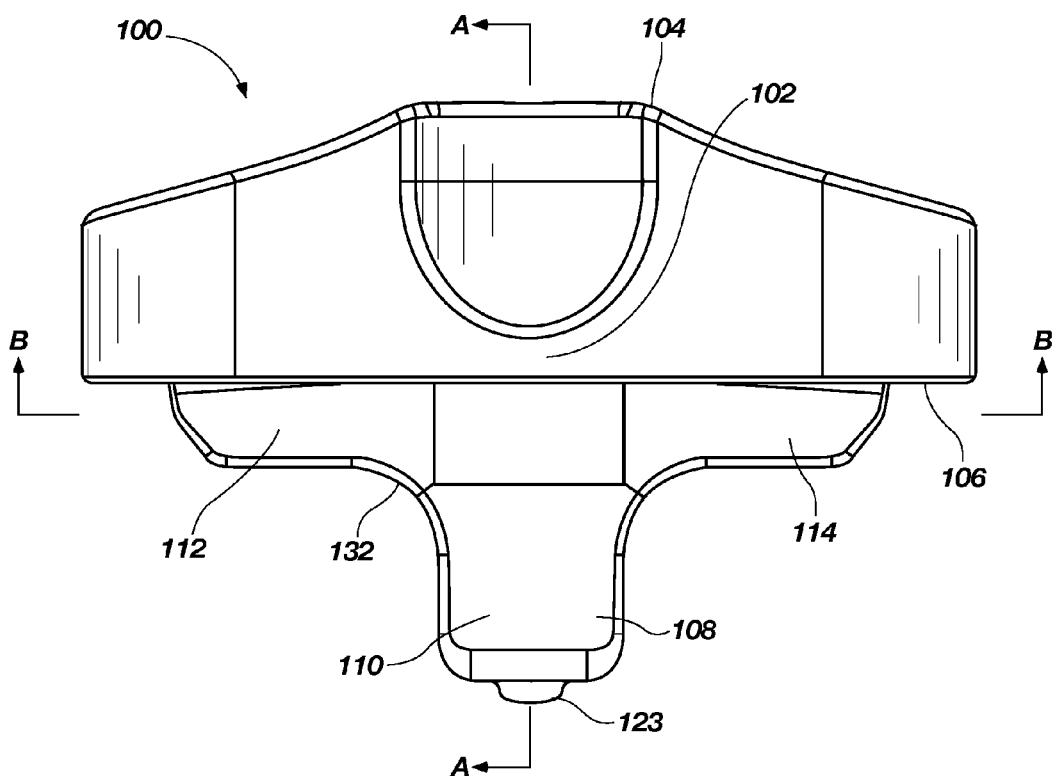
FIG. 1B is a front view of the tibial component shown in FIG. 1A.

Referring now to FIGS. 1A and 1B, there is depicted a front view of a tibial component 100 according to an embodiment of the present disclosure. The tibial component 100 may be formed entirely of a plastic, such as polyethylene. In an embodiment, the tibial component 100 may be formed of any elastohydrodynamic material, including PEEK and polycarbonate urethane (PCU) and hard bearing material such as ceramics and diamond surfaces. In an embodiment of the present disclosure, the tibial component 100 may be of unitary construction. In an embodiment, the tibial component 100 may be formed from disparate pieces.

The tibial component 100 may include a bearing body 102 having an articulating or bearing surface 104 and a tibial tray 106. The articulating surface 104 of the tibial component 100 may be configured for receiving a head of a femoral component (not shown) or the head of a natural femur. In particular, the articulating surface 104 may comprise a first concave bearing surface 104A and a second concave bearing surface 104B for receiving artificial, or natural, femur condyles.

In an embodiment of the present disclosure, the articulating surface 104 may be an ultracongruent bearing surface. The tibial tray 106 may be bonded with bone cement to a tibial plateau of a tibia that has been previously prepared. (Typically, tibia preparation involves resecting the proximal end of the tibia.)

Extending downwardly from the tibial tray 106 may be a stem 108. As best seen in FIG. 1B, the stem 108 may include a primary stem portion 110 and a pair of medial-lateral wing portions 112 and 114. The wing portions 112 and 114 may extend laterally on either side of the primary stem portion 110. The primary stem portion 110 may extend a greater distance below the tibial tray 106 of the tibial component 100 than the wing portions 112 and 114.

Figure 2:
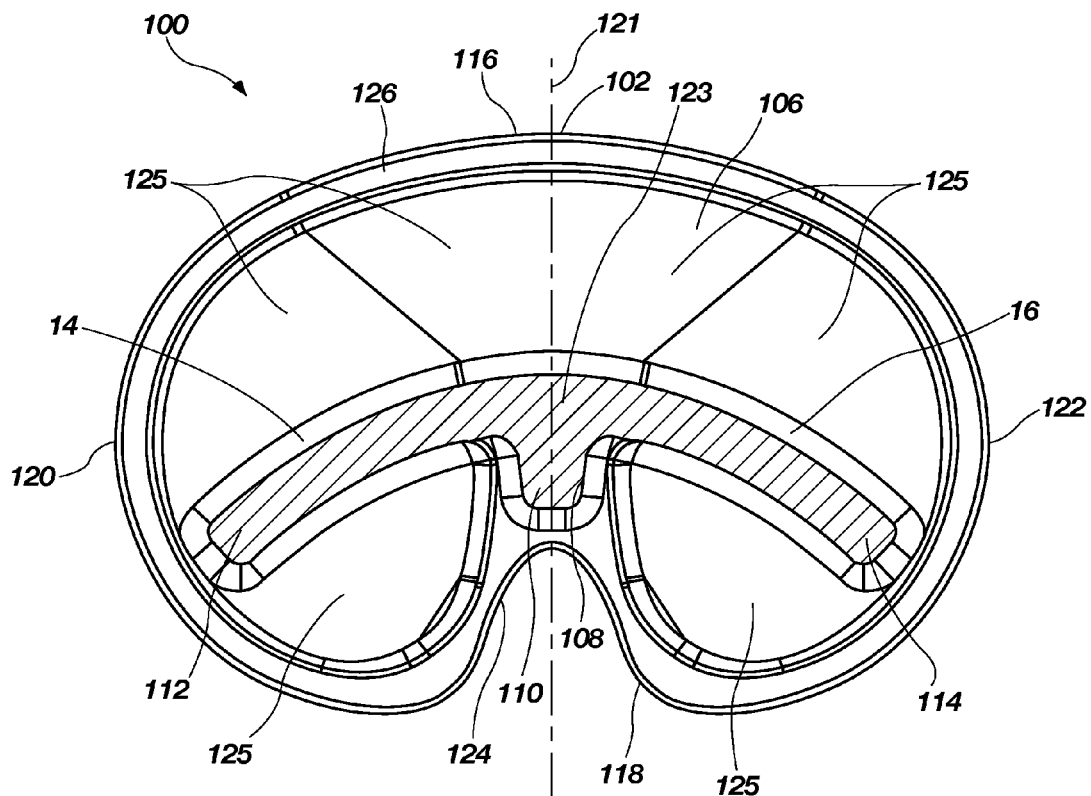
FIG. 2 is a bottom view of the tibial component shown in FIG. 1A.

Referring now to FIG. 2, there is depicted a cross-sectional view of the tibial component 100 taken along the cross-section B-B shown in FIG. 1B, where like reference numerals depict like components. The tibial component 100 may include an anterior portion 116 and a posterior portion 118 separated by a pair of opposing side portions 120 and 122.

As can be observed in FIG. 2, the cross-sectional geometry of the primary stem portion 110 may include a T-shaped portion 123 to provide improved torsional resistance when the stem 108 is implanted into a tibia. (The T-shaped nature of the primary stem portion 110 can also be observed in FIG. 1B.) That is, the T-shaped cross-section of the primary stem portion 110 may resist torsional forces exerted on the tibial component 100 during in-vivo loading.

As can be further observed in FIG. 2, in an embodiment of the present disclosure, the wing portions 112 and 114 of the stem 108 may be arcuate. In particular, the wing portions 112 and 114 of the stem 108 may curve toward the posterior portion 118 of the tibial component 100 as they extend laterally away from the primary stem portion 110 and an anterior-posterior plane 121 bisecting the component 100. In an embodiment of the present disclosure, the wing portions 112 and 114 may extend beneath the most concave points of the articulating surface 104, 104A and 104B, to thereby provide optimal support to the knee joint.

In an embodiment of the present disclosure, the wing portions 112 and 114 may have a thickness of about 0.118 inches to 0.236 inches (3 mm to 6 mm). In addition, the posterior portion 118 of the tibial component 100 may include a cutout 124 for accommodating tissue, such as a patient's posteriorcruciate ligament (not shown). Thus, the cutout 124 may reduce the need for tissue resection. In addition, the cutout 124 may provide a visual observation point for excess cement removal and for bony osteophyte removal, if needed. The wing portions 112 and 114 may each include an anterior facing surface 142. The anterior facing surfaces 142 may be convex.

Figure 2A:
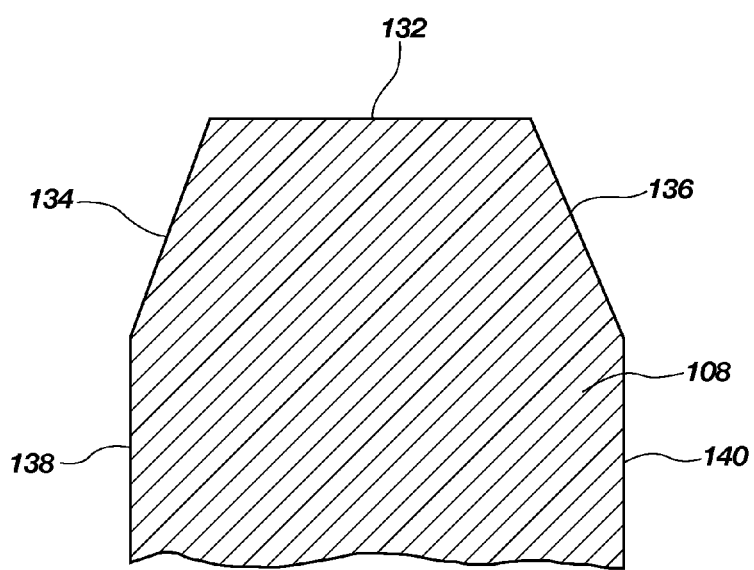
FIG. 2A is a cross-sectional view of a terminating edge of a stem.

Referring now to FIGS. 1B and 2A, a terminating surface 132 of the stem 108, including the primary stem portion 110 and the wing portions 112 and 114, may include chamfered portions 134 and 136 connecting sides 138 and 140, respectively, to the terminating surface 132. The intersection between side 138 and the chamfered portion 134, and the chamfered portion 134 and terminating surface 132 may be angular or rounded. The intersection between side 140 and the chamfered portion 136, and the chamfered portion 136 and terminating surface 132 may also be angular or rounded. It will be appreciated that the chamfer may reduce the occurrence of cortical bone impingement while maximizing load carrying capacity.

Figure 3:
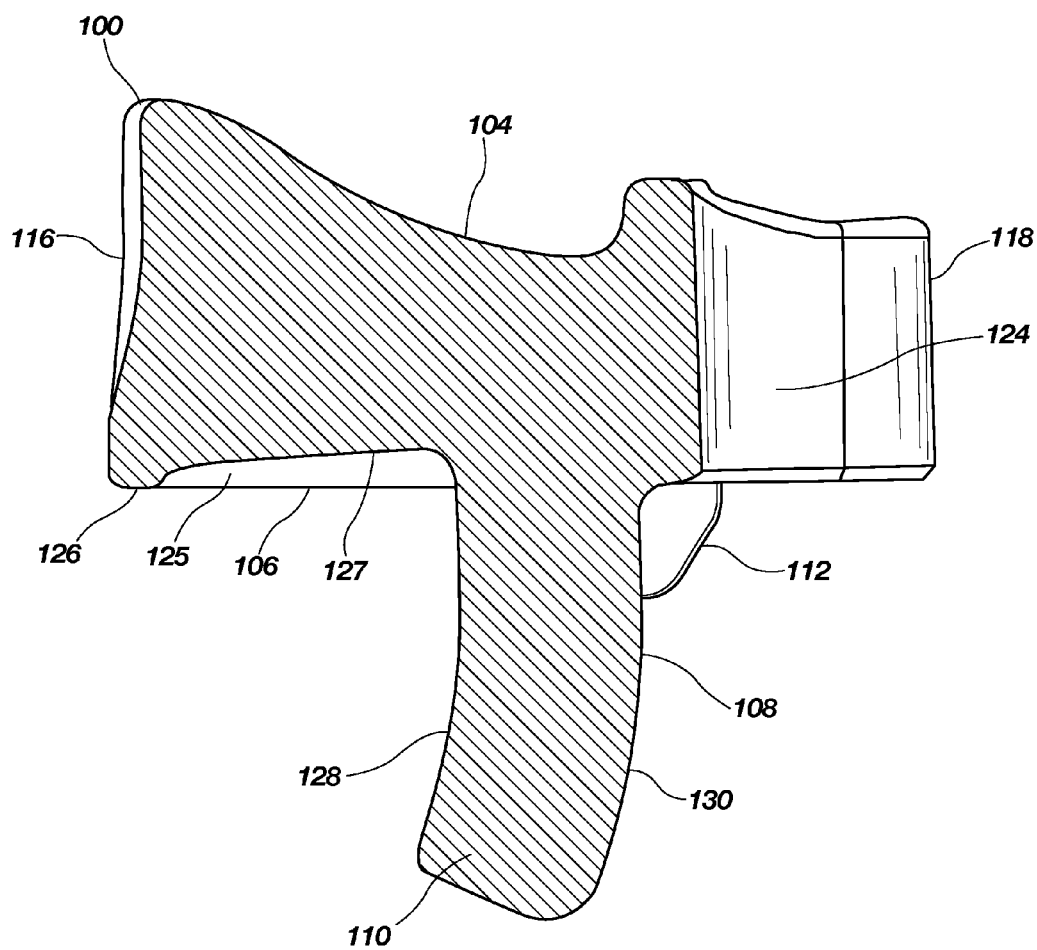
FIG. 3 is a cross-sectional view of the tibial component shown in FIG. 1A.

Referring now to FIG. 3, there is depicted a cross-sectional view of the tibial component 100 taken along the cross-section A-A shown in FIG. 1B, where like reference numerals depict like components. The primary stem portion 110 may extend downwardly from an inferior surface 125 of the tibial tray 106. A first portion 110A of the primary stem portion 110 may extend relatively straight down from the interior surface 125. A second portion 110B of the primary stem portion 110 may follow the first portion 110A and terminate at a free end 110C.

The second portion 110B of the primary stem portion 110 may include a curvature. In an embodiment of the present disclosure, the second portion 110B of the primary stem portion 110 may curve anteriorly, i.e., towards the anterior portion 116 of the tibial component 100 as it extends downwardly. In particular, the second portion 110B may comprise an anteriorly facing surface 128 that may be concave and a posteriorly facing surface 130 that may be convex. The anterior facing surface 128 may be referred to herein as an anterior curve forming a concave, anterior-facing space 131.

In an embodiment of the present disclosure, a cross-section of the stem 108 may have an anterior curvature in the anterior-posterior plane 121. Thus, it will be appreciated that an embodiment of the present disclosure may comprise a stem having an anteriorly curved stem portion and posteriorly curved medial-lateral wing portions.

The second portion 110B of the primary stem portion 110 may include a radius of curvature indicated by the arrow marked with the reference numeral 113. In an embodiment of the present disclosure, the radius of curvature 113 may be selected from one of 1.131 inches (2.872 cm), 1.167 inches (2.964 cm), 1.202 inches (3.053 cm), 1.246 inches (3.164 cm), 1.291 inches (3.279 cm), 1.336 inches (3.393 cm), and 1.380 inches (3.505 cm). In an embodiment of the present disclosure, the radius of curvature 113 may be between 0.75 inches and 1.75 inches (1.905 cm and 4.445 cm). In an embodiment of the present disclosure, the radius of curvature 113 may be between 1.0 inch and 1.4 inches (2.54 cm and 3.556 cm).

The first portion 110A of the primary stem portion 110 may include a length marked with the reference numeral 115. In an embodiment of the present disclosure, the length 115 may be between about 0.25 inches and 0.75 inches (0.635 cm and 1.905 cm). In an embodiment, the length 115 may be about 0.407 inches (1.033 cm).

In an embodiment of the present disclosure, the primary stem portion 110 may extend from the inferior surface 125 to the free end 110C at a length indicated by the double arrows indicated by the reference numeral 117. In an embodiment of the present disclosure, the length 117 may be between about 0.6 inches and 1.5 inches (1.524 cm and 3.81 cm). In an embodiment, the length 117 may be one of 0.755 inches (1.917 cm), 0.798 inches (2.026 cm), 0.842 inches (2.138 cm), 0.895 inches (2.273 cm), 0.948 inches (2.407 cm), 1.001 inches (2.542 cm), and 1.055 inches (2.679 cm). In an embodiment, the length 117 may be between 0.393 inches and 1.968 inches (1 cm and 5 cm).

In an embodiment of the present disclosure, the primary stem portion 110 may be offset from an anterior-most edge 139 of the anterior portion 116 by a length indicated by the double arrows marked with the reference numeral 119. In an embodiment, the length 119 may be between about 0.5 inches and 1.25 inches (1.27 cm and 3.175 cm). In an embodiment, the length 119 may be one of 0.647 inches (1.643 cm), 0.683 inches (1.734 cm), 0.718 inches (1.823 cm), 0.763 inches (1.938 cm), 0.807 inches (2.049 cm), 0.852 inches (2.164 cm), and 0.896 inches (2.275 cm).

As can be seen in FIGS. 2 and 3, the inferior surface 125 may comprise a concave portion 127. It will be appreciated that the concave portion 127 of the inferior surface 125 may provide an increased bonding area as compared to conventional flat surfaces that are found in previously available tibial components. The concave portion 127 may form a convex or conical bone cement mantle when the tibial component 100 is bonded onto a prepared surface of a tibia. The tibial tray 106 may also include a flat-surface portion or rim 126 that extends below and around the entire perimeter of the concave portion 127 of the inferior surface 125. The flat-surface portion or rim 126 may allow cortical coverage with respect to the tibia (not shown) and may be about 0.1 inches (2.6 mm) in width.

The concave portion 127 varies in height (height variation being an inherent feature of concavity) and may have a largest height which, when measured from the bottom surface of the rim 126 is indicated by the double arrows marked with the reference numeral 129 in FIG. 3. In an embodiment, the largest height 129 of the concave portion 127 may be between 0.019 inches and 0.196 inches (0.5 mm and 5 mm). Thus, it will be appreciated that a corresponding largest height of the convex or conical bone cement mantle formed under the concave portion 127 may be referred to as having a thickness of about 0.019 inches and 0.196 inches (0.5 mm and 5 mm).

Figure 4A:
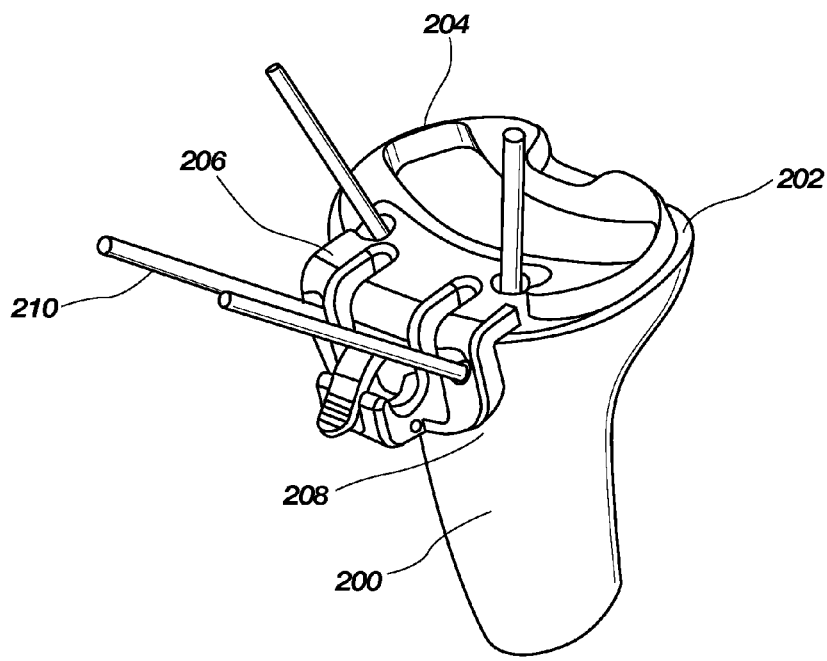
FIGS. 4A-4G depict a process of installing the tibial component shown in FIG. 1A into a tibia.
Figure 4B:
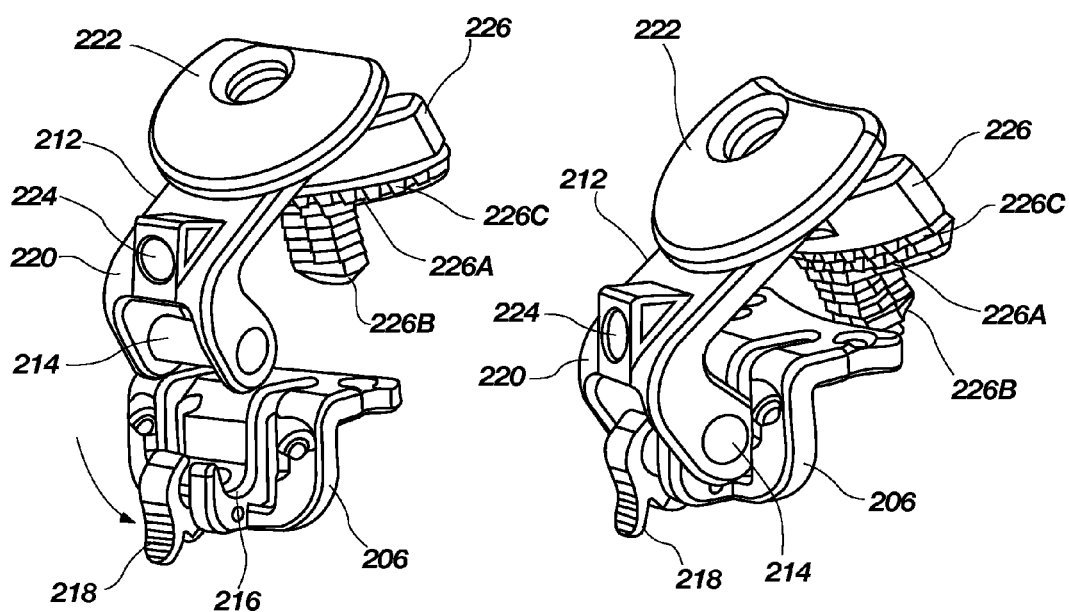

Referring now to FIGS. 4A-4G, there is depicted a tool and method for installing the tibial component 100 into a proximal end of a tibia pursuant to an embodiment of the present disclosure. Referring to FIG. 4B, there is depicted a tool 198 for forming a cavity in a bone. The tool 198 may include a block portion 206 and a pivot arm 220. The block portion 206 may be L-shaped and include a first portion 206A and a second portion 206B. The first portion 206A and the second portion 206B may form a ninety-degree angle with respect to each other. The first portion 206A and the second portion 206B of the block portion 206 may include each include a pair of guide holes 215.

The pivot arm 220 may be L-shaped. The pivot art 220 may include a first portion 220A and a second portion 220B. The first portion 220A and the second portion 220B may form a ninety-degree angle with respect to each other. The second portion 220B may include a pair of spaced apart members 223. Extending between the spaced apart member 223 may be a shaft 214. Disposed on the first portion 220A may be a tool receptacle or socket 224 for receiving a shaft of a handle. Also disposed on the first portion 220A is an impact head 222. Extending downward from the first portion 220A may be a punch 226 that corresponds in shape and size to the stem of a tibial component. For example, the punch 226 may correspond in shape and size to the stem 108 of the tibial component 100. The punch may include an end portion 226A that corresponds in shape and size to that of the stem 108 of the tibial component 100. In particular, the end portion 226A may include stem portion 226B that includes a curvature corresponding to that of the primary stem portion 110 of the stem 108. This means that stem portion 226 may have an anterior curve forming a concave, anterior-facing space, and may have a radius of curvature of between 0.75 inches and 1.75 inches, and may have a length of curvature of between 0.393 inches and 1.968 inches, and may have an anterior-posterior position of between 0.5 inches and 1.25 inches, and the latter may also be states as follows: the stem may have an anterior surface that is offset from an anterior-most edge of the anterior portion of the tibial component by a length of between 0.5 inches and 1.25 inches. Wing portions 226C may also extend laterally from the stem portion 226B similar to wings 112 and 114 of the stem 108. As will be explained in more detail hereinafter, the punch 226 may be used to form a cavity in a prepared surface of a tibia.

The second portion 206B of the pivot block 206 may include a seat 216 for receiving the shaft 214. A latch 218 may secure the shaft 214 in the seat 216. With the shaft 214 secured in the seat 216, the pivot arm 220 may pivotally rotate.

Referring now to FIGS. 4A, 4C-4G, a procedure of implanting the tibial component 100 onto an end of a tibia will be disclosed. Referring to FIG. 4A, a tibia 200 may first be resected to provide a prepared surface 202 on the tibial plateau as is known to one having ordinary skill in the art. A template 204 may then be secured onto the surface 202. The template 204 may indicate the location of the cavity for receiving the stem 108 of the tibial component 100.

The pivot block 206 may then be installed to an anterior portion 208 of the tibia 200. The pivot block 206 may be secured to the tibia 200 using pins or screws 210 installed into the guide holes 215.

Figure 4C:
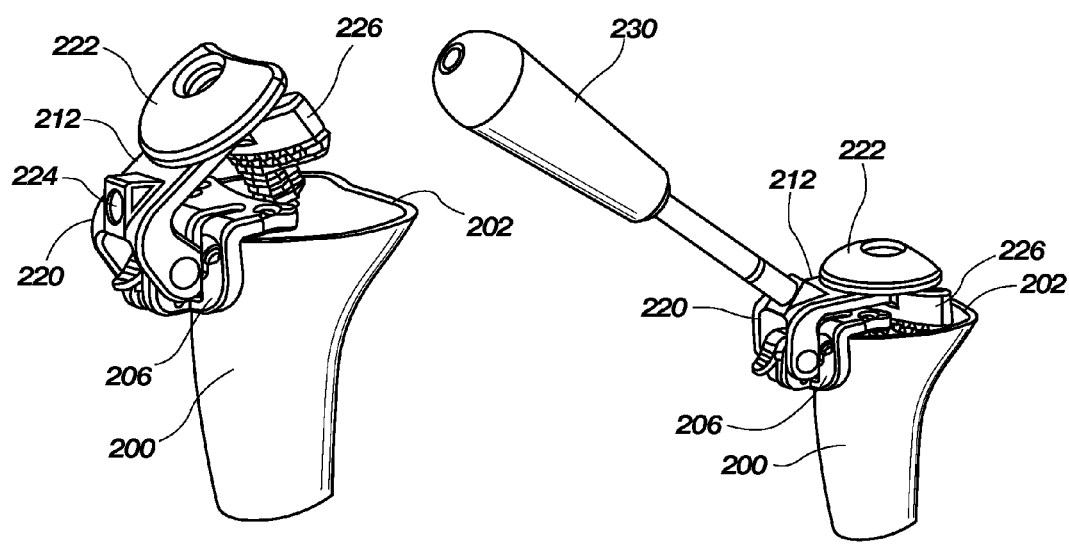
Figure 4D:
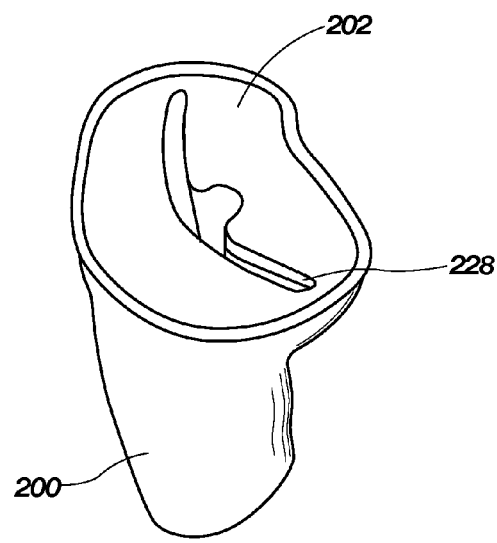

As shown in FIGS. 4C and 4D, when the pivot arm 220 is installed into the pivot block 206, a surgeon may form a cavity 228 in the prepared surface 202 of the tibial plateau by impacting the impact head 222 on the pivot arm 220 with a tool. Optionally, the surgeon may insert a handle 230 into the tool receptacle 224 to provide additional stability and leverage. The cavity 228 is formed as the punch 226 is rotatably driven into the tibial plateau 202 by the force of the impact. Because the punch 226 is mounted to the pivot arm 220, it will be appreciated that the punch 226 is rotatably driven into the prepared surface 202 along an arcuate path.

Figure 4E:
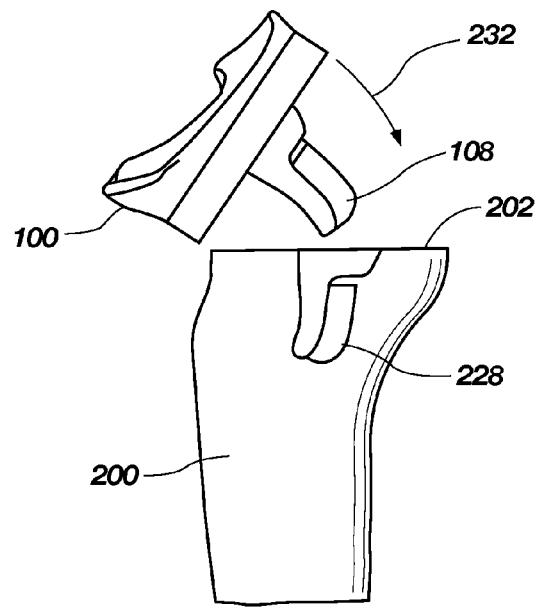
Figure 4F:
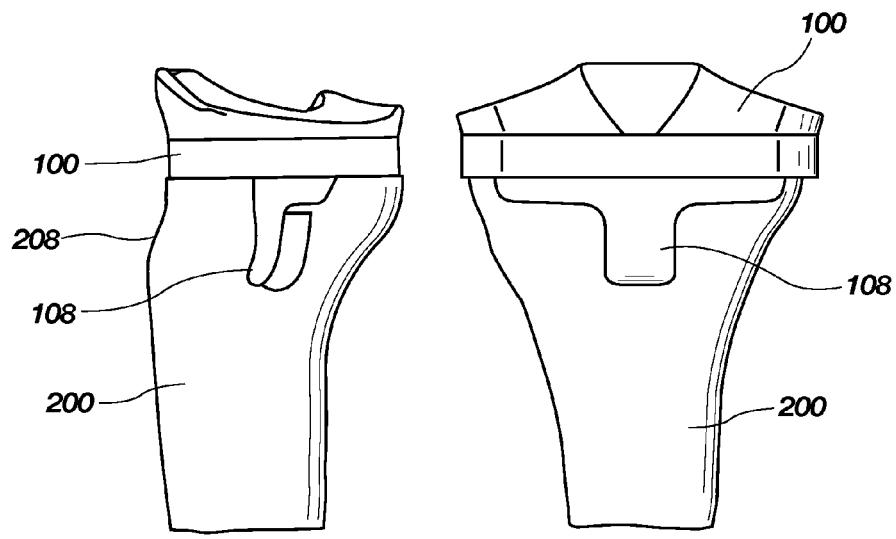
Figure 4G:
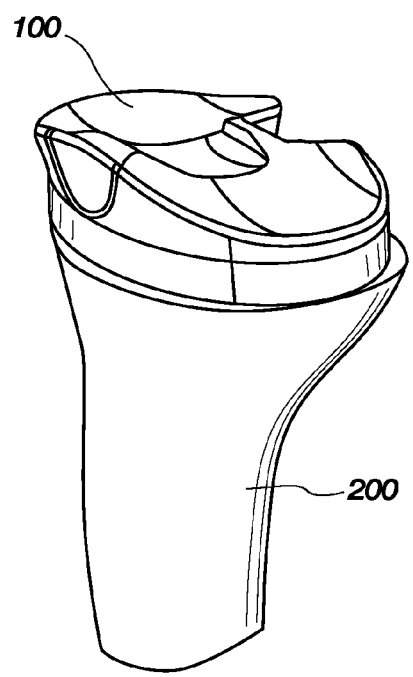

As shown in FIGS. 4E-4G, the stem 108 of the tibial component 100 may be inserted into the cavity 228 formed in the tibial plateau 202 by the punch 226. It will be noted that the stem 108 may be rotatably inserted into the cavity 228 as shown by the arrow indicated with the reference numeral 232. The cavity 228 may extend from the surface 202 downwardly, with an anterior curvature.

It will be appreciated that the ability to rotatably install the stem 108 into the cavity 228 requires less resection and displacement of surrounding tissue as compared to stems that must be vertically inserted into cavities. Further, as perhaps best seen in FIG. 4F, when installed, the stem 108 of the tibial component 100 curves anteriorly, i.e., towards the anterior portion 208 of the tibia 200.

Figure 5:
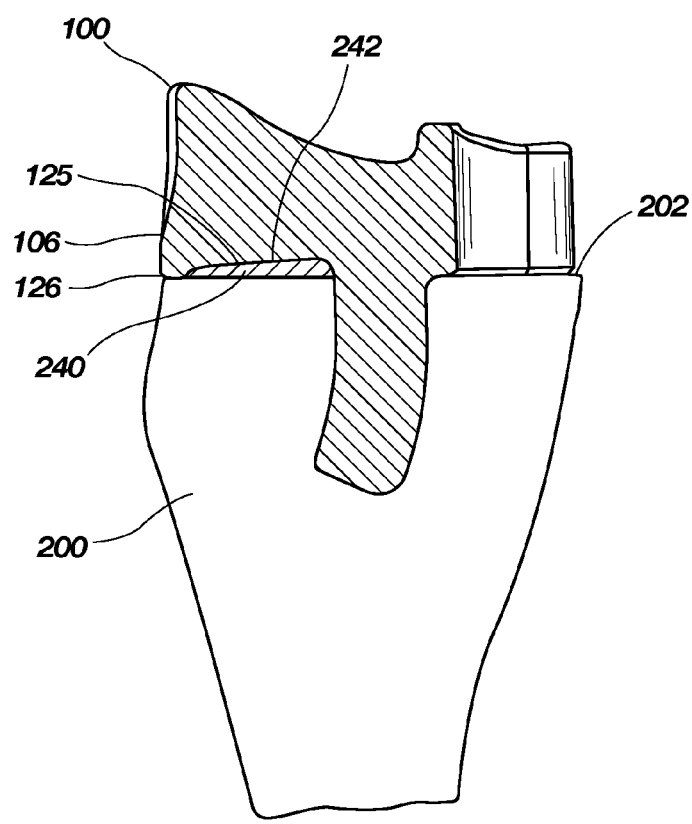
FIG. 5 depicts a cross-sectional view of a tibial component installed onto a tibia.

Referring now to FIG. 5, the tibial component 100 may be secured to the tibia 200 by bone cement 240. In particular, the bone cement 240 may be applied between the inferior surface 125 of the tibial tray 106 of the tibial component 100 and the prepared surface 202. Because of the concave nature of the inferior surface 125 of the tibial tray 106, the cement mantle 242 may include a top surface that is convex or conical. The concave inferior surface 125 may produce lower stress in the cement mantle 242 under in-vivo loading. The bone cement 240 may also be utilized to secure the stem 108 into the cavity 228.

Those having ordinary skill in the relevant art will appreciate the advantages provide by the features of the present disclosure. For example, it is a feature of the present disclosure to provide a tibial component that provides low stress in the cement mantle during in-vivo loading. Another feature of the present disclosure to provide a tibial component with an anterior curved stem.

In the foregoing Detailed Description, various features of the present disclosure are grouped together in a single embodiment for the purpose of streamlining the disclosure. This method of disclosure is not to be interpreted as reflecting an intention that the claimed disclosure requires more features than are expressly recited. Rather, inventive aspects lie in less than all features of a single foregoing disclosed embodiment.

It is to be understood that the above-described arrangements are only illustrative of the application of the principles of the present disclosure. Numerous modifications and alternative arrangements may be devised by those skilled in the art without departing from the spirit and scope of the present disclosure and the appended claims are intended to cover such modifications and arrangements. Thus, while the present disclosure has been shown in the drawings and described above with particularity and detail, it will be apparent to those of ordinary skill in the art that numerous modifications, including, but not limited to, variations in size, materials, shape, form, function and manner of operation, assembly and use may be made without departing from the principles and concepts set forth herein.

What is claimed:

1. A tibial component for use in a knee replacement surgery, said tibial component having an anterior portion and a posterior portion, the tibial component comprising:
    a bearing surface for receiving a femoral component attached to an end of a femur bone;
    an inferior surface opposite said bearing surface; and
    a stem extending downwardly and anteriorly from said inferior surface to a terminal end, such that the stem includes an anterior curvature in a sagittal plane, wherein said stem includes an anteriorly facing surface which is posteriorly curved, and wherein the anteriorly facing surface is convex in a transverse plane, and wherein the stem also includes an posteriorly facing surface which is posteriorly curved, and wherein the posteriorly facing surface is concave in a transverse plane.

2. The tibial component of claim 1, further comprising an anterior to posterior plane, wherein said anterior curvature lies in the anterior to posterior plane.

3. The tibial component of claim 1, wherein the anterior curvature has a radius of curvature of between 0.75 inches and 1.75 inches.

4. The tibial component of claim 1, wherein the anterior curvature has a radius of curvature of between 1.0 inch and 1.4 inches.

5. The tibial component of claim 3, wherein the stem comprises a length of between 0.393 inches and 1.968 inches and wherein an anterior surface of the stem is offset from an anterior-most edge of the anterior portion of the tibial component by a length of between 0.5 inches and 1.25 inches.

6. The tibial component of claim 1, wherein said bearing surface comprises a first concave bearing surface and a second concave bearing surface.

7. The tibial component of claim 1, wherein said stem comprises a T-shaped cross-section.

8. The tibial component of claim 1, further comprising a body portion, wherein said bearing surface is formed on a top surface of the body portion and said inferior surface is formed on a bottom surface of the body portion.

9. The tibial component of claim 8, wherein said body portion is of unitary construction.

10. The tibial component of claim 9, wherein said body portion comprises polyethylene.

11. The tibial component of claim 1, wherein said stem further comprises a terminal end, wherein said anteriorly facing surface extends between said inferior surface and said terminal end.

12. The tibial component of claim 11, wherein said anteriorly facing surface comprises a concave portion.

13. The tibial component of claim 1, wherein said stem comprises a terminal edge and an anteriorly facing surface, wherein said stem further comprises a tapered portion interposed between said terminal edge and said anteriorly facing surface.

14. A tibial component for use in a knee replacement surgery, said tibial component having an anterior portion and a posterior portion, the tibial component comprising:
a bearing surface for receiving a femoral component attached to an end of a femur bone;
an inferior surface opposite said bearing surface;
a stem extending downwardly from said inferior surface, wherein said stem includes an anterior curvature in a substantially vertical plane and said stem also includes an anteriorly facing surface that is convex in a substantially horizontal plane and a posteriorly facing surface that is concave in the substantially horizontal plane, wherein the vertical plane is substantially perpendicular to the horizontal plane; and
said stem having a primary stem portion extending a total downward length of the stem and a pair of laterally and posteriorly extending wing portions, wherein each of the pair of wing portions extends less than a majority of the total downward length of the stem.

15. The tibial component of claim 14, further comprising an anterior to posterior plane bisecting said tibial component, wherein said pair of wing portions extend laterally and posteriorly from said anterior to posterior plane.

16. The tibial component of claim 14, wherein said wing portions each comprise a posterior curvature.

17. The tibial component of claim 14, wherein said bearing surface comprises a first concave bearing surface and a second concave bearing surface.

18. The tibial component of claim 14, wherein said stem further comprises a T-shaped cross-section.

19. The tibial component of claim 14, further comprising a body portion, wherein said bearing surface is formed on a top surface of the body portion and said inferior surface is formed on a bottom surface of the body portion.

20. The tibial component of claim 19, wherein said body portion is of unitary construction.

21. The tibial component of claim 19, wherein said body portion comprises polyethylene.

22. The tibial component of claim 14, wherein said anteriorly facing surface comprises a concave portion.

23. The tibial component of claim 22, wherein the anteriorly facing surface has a radius of curvature of between 0.75 inches and 1.75 inches.

24. The tibial component of claim 22, wherein the anteriorly facing surface has a radius of curvature of between 1.0 inch and 1.4 inches.

25. The tibial component of claim 22, wherein the stem comprises a length of between 0.393 inches and 1.968 inches and wherein the anteriorly surface of the stem is offset from the anterior portion of the tibial component by a length of between 0.5 inches and 1.25 inches.

26. A tibial component for use in a knee replacement surgery, said tibial component having an anterior portion and a posterior portion, the tibial component comprising:
a bearing surface for receiving a femoral component attached to an end of a femur bone;
an inferior surface opposite said bearing surface, said inferior surface comprising a concave portion; and
a stem extending downwardly and anteriorly, forming an anterior curvature, from said inferior surface, wherein said stem includes an anteriorly facing surface which is posteriorly curved, such that the anteriorly facing surface is curved in a direction that is opposite to the anterior curvature of the stem, and wherein said stem also includes a posteriorly facing surface which is posteriorly curved, such that the posteriorly facing surface is curved in a direction that is opposite to the anterior curvature of the stem.

27. The tibial component of claim 26, further comprising a rim circumscribing at least a portion of said concave portion.

28. The tibial component of claim 26, further comprising an anterior to posterior plane, wherein said anterior curvature lies in the anterior to posterior plane.

29. The tibial component of claim 26, wherein said bearing surface comprises a first concave bearing surface and a second concave bearing surface.

30. The tibial component of claim 26, wherein said stem comprises a T-shaped cross-section.

31. The tibial component of claim 26, further comprising a body portion, wherein said bearing surface is formed on a top surface of the body portion and said inferior surface is formed on a bottom surface of the body portion.

32. The tibial component of claim 31, wherein said body portion is of unitary construction.

33. The tibial component of claim 31, wherein said body portion comprises polyethylene.

34. The tibial component of claim 26, wherein said concave portion of the inferior surface has a varying height which, at its largest, is, between 0.019 inches and 0.196 inches.

35. A tibial component for use in a knee replacement surgery, said tibial component having an anterior portion, posterior portion and an anterior to posterior plane bisecting said tibial component, the tibial component comprising:
a bearing surface for receiving a femoral component attached to an end of a femur bone;
said bearing surface comprising a first concave bearing surface and a second concave bearing surface;
an inferior surface opposite said bearing surface, said inferior surface comprising a concave portion and a rim circumscribing at least a portion of said concave portion;
a stem comprising a first portion extending downwardly and anteriorly from said inferior surface to a terminal end, such that a proximal portion of the stem extends substantially straight down from said inferior surface, said proximal portion forming a posterior curvature in a transverse plane, and a distal portion of the stem forms an anterior curvature in a sagittal plane;
said stem comprising a terminal edge;

a cross-section of said first portion of the stem having an anterior curvature in the anterior to posterior plane;

said first portion of the stem comprising an anteriorly facing surface having a concave shape, wherein said anteriorly facing surface is posteriorly curved, and wherein said first portion of the stem also comprises a posteriorly facing surface having a concave shape, wherein said posteriorly anteriorly facing surface is posteriorly curved;

said first portion of the stem further comprising a T-shaped cross-section;

said stem further comprising a primary stem portion extending a total downward length of the stem and a pair of wing portions extending laterally and posteriorly from said anterior to posterior plane, wherein each of the pair of wing portions extends less than a majority of the total downward length of the stem;

each of said wing portions having an anteriorly facing surface having a concave shape;

a body portion;

a cutout in a posterior region of the body portion;

said body portion being of unitary construction; and said body portion comprising polyethylene;

wherein said bearing surface is formed on a top surface of the body portion and said inferior surface is formed on a bottom surface of the body portion;

wherein said stem further comprises a tapered portion interposed between said terminal edge and said anteriorly facing surface;

wherein said concave portion of the inferior surface has a varying height which, at its largest, is, between 0.019 inches and 0.196 inches;

wherein the anterior curvature has a radius of curvature between 0.75 inches and 1.75 inches;

wherein the stem comprises a length of between 0.393 inches and 1.968 inches; and wherein the anteriorly facing surface of the first portion of the stem is offset from an anterior-most edge of the anterior portion of the tibial component by a length of between 0.5 inches and 1.25 inches.

36. The tibial component of claim 1, said stem further comprising:

a primary stem portion extending a total downward length of the stem and a pair of wing portions extending laterally and posteriorly from said anterior to posterior plane, wherein each of the pair of wing portions extends less than a majority of the total downward length of the stem.

37. The tibial component of claim 26, said stem further comprising:

a primary stem portion extending a total downward length of the stem and a pair of wing portions extending laterally and posteriorly from said anterior to posterior plane, wherein each of the pair of wing portions extends less than a majority of the total downward length of the stem.

38. The tibial component of claim 14, wherein the pair of wing portions and the primary stem portion form a stepped shape in the lateral direction.

* * * * *